(12) United States Patent
Pedrazzini

(10) Patent No.: US 9,314,796 B2
(45) Date of Patent: Apr. 19, 2016

(54) LOADING AND UNLOADING BENCH FOR LOADING AND UNLOADING RACKS OF BIOLOGICAL MATERIAL IN AN AUTOMATION INSTALLATION

(75) Inventor: Gianandrea Pedrazzini, Paradiso (CH)

(73) Assignee: INPECO HOLDING LTD., Valletta (MT)

( * ) Notice: Subject to any disclaimer, the term of this patent is extended or adjusted under 35 U.S.C. 154(b) by 342 days.

(21) Appl. No.: 13/057,584

(22) PCT Filed: Jul. 13, 2009

(86) PCT No.: PCT/EP2009/058886
§ 371 (c)(1),
(2), (4) Date: Feb. 4, 2011

(87) PCT Pub. No.: WO2010/015486
PCT Pub. Date: Feb. 11, 2010

(65) Prior Publication Data
US 2011/0158850 A1  Jun. 30, 2011

(30) Foreign Application Priority Data
Aug. 5, 2008  (IT) .............................. MI2008A1469

(51) Int. Cl.
G01N 35/04 (2006.01)
B01L 9/02 (2006.01)
B01L 9/06 (2006.01)

(52) U.S. Cl.
CPC ... *B01L 9/02* (2013.01); *B01L 9/06* (2013.01); *G01N 35/04* (2013.01); *B01L 2200/025* (2013.01); *B01L 2300/022* (2013.01); *G01N 2035/0422* (2013.01); *G01N 2035/0465* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,982,553 | A * | 1/1991 | Itoh | 53/246 |
| 5,603,160 | A * | 2/1997 | Lessard et al. | 29/896.62 |
| 5,985,215 | A * | 11/1999 | Sakazume et al. | 422/67 |
| 6,177,050 | B1 | 1/2001 | Bybee et al. | |
| 6,843,357 | B2 * | 1/2005 | Bybee et al. | 198/345.3 |
| 2002/0119077 | A1 * | 8/2002 | Shumate et al. | 422/100 |
| 2002/0197722 | A1 | 12/2002 | Fichera et al. | |
| 2005/0036907 | A1 | 2/2005 | Shoji | |
| 2006/0210431 | A1 * | 9/2006 | Higuchi et al. | 422/63 |
| 2006/0216198 | A1 | 9/2006 | Koike | |

* cited by examiner

*Primary Examiner* — P. Kathryn Wright
(74) *Attorney, Agent, or Firm* — Birch, Stewart, Kolasch & Birch, LLP

(57) ABSTRACT

An apparatus for loading/unloading test tubes which includes a bench for conveying one or more racks of test-tubes, a device for sequentially stopping the racks of test tubes for loading and unloading the test tubes from the rack, an emitter which is positioned to detect the presence of the test tubes in each row of the rack and a transport device and handling device for moving test tubes between the test tube rack and the transport device.

2 Claims, 4 Drawing Sheets

LOADING AND UNLOADING BENCH FOR LOADING AND UNLOADING RACKS OF BIOLOGICAL MATERIAL IN AN AUTOMATION INSTALLATION

The present invention relates to a loading and unloading bench for loading and unloading racks of biological material in an automated transport installation, so as to enable the processed samples to be tracked and said samples to be possibly reloaded in the installation.

The development of laboratory medicine that has been observed over the last twenty years has led the analysis laboratories to favour the use of machines designed to automate laboratory examinations, obtaining various advantages such as speeding up examinations and greater security for laboratory workers, who, having simply to manage the machines, are increasingly less involved in the direct handling of potentially infected biological materials to be analysed.

Automation is defined as the use of a set of devices having the function of processing the biological materials, which are reachable by means of a conveyor belt that is part of the installation, managing the processing thereof and memorizing the life cycle thereof.

Once the required analyses have been conducted on a set biological sample, the need may arise to conduct further analyses thereupon so as to validate the analysis reports thereof or to conduct new checks.

It is thus important to be able to ensure the traceability of a sample inside the laboratory, and in the case of use of automation, inside the automatic installation, whether it is still moving on the conveyor belts or whether it has been positioned in suitable unloading installations.

If, after the analyses have been conducted, a sample of biological material has to be conserved for a medium to long period, refrigerated conserving installations are generally used that are suitable for enabling the biological materials to be traceable and recoverable when required, as disclosed in Italian Patent Publication No. 1385292 issued on Jan. 11, 2011.

On the other hand, when a further analysis of the sample might be required in a short time or in the case of small laboratories that do not make use of refrigerated conserving installations, unloading benches for unloading samples of biological materials can be used. Such benches, however, envisage that the operator, in the event of further analyses being required, manually traces the sample to be loaded into the installation, an operation that partially eliminates the benefits obtained from using automation, both in terms of time and of security, both for the operator, and for the test tube containing the sample of biological material.

The object of the present invention is to provide analysis laboratories with an automated workbench from which to load, by means of a suitable device, the racks of biological material to be analysed into the automatic transport installations, and into which to unload such racks, upon completion of the analyses, onto said bench in known positions so as to enable the analyses to be traceable and to enable the analyses to be subsequently possibly reprocessed in the automation installation, so as to overcome the problems disclosed above.

According to the invention, the object is achieved with an automated bench for loading/unloading test tubes by means of a device for moving test tubes between multi-location test-tube racks arranged according to parallel rows lying on said workbench and devices for conveying single test tubes that are movable on an automatic test-tube conveyor, characterized in that it comprises means for transferring said multi-location racks towards a test tubes load/unload position, and an ordered succession of pistons that are selectively mobile between a lowered rest position and a raised stop position for said rack, the pistons being positioned on the bench in such a manner as to stop the rack in successive positions, i.e. with rows of rack that occupy in succession said bench load/unload position, a bench sensor detecting the presence of test tubes in every single row of rack in the load/unload position.

Such load/unload bench comprising a control unit capable of memorizing the codes identifying the test tubes and the corresponding positions when the test tubes are unloaded into the multi-location racks on the test-bench, thus making such test tubes traceable and reloadable into the automation installation, when required.

This bench has been designed for the purpose of enabling the test tubes processed in an automation installation to have, upon completion of the analyses, a parking space, and to enable the test tubes to be automatically traced in such a space to be reloaded into the installation so as to avoid as far as possible human intervention.

These and other features of the present invention will be made clearer by the following detailed description of a practical embodiment thereof illustrated by way of non-limiting example in the attached drawings, in which.

Figure 1:
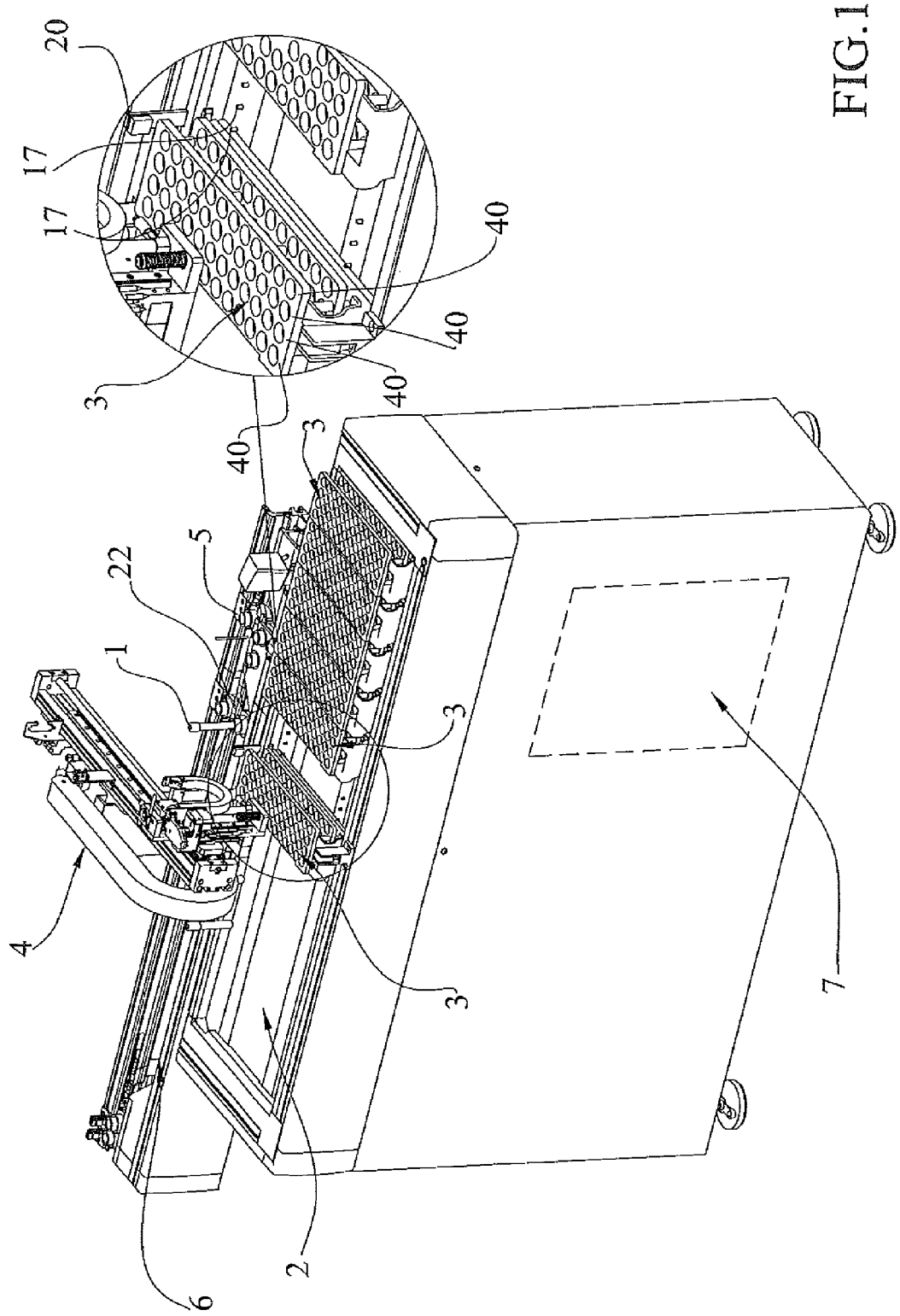
FIG. 1 shows a perspective view of the bench that is the object of the present invention with a portion on an enlarged scale.

In FIG. 1 there is shown an apparatus for loading/unloading test tubes 1 positioned on a bench 2 in suitable multi-location racks 3 and comprising a test-tube handling device 4, having the role of moving said test tubes 1 from the racks 3 to suitable transport devices 5 for a single test tube, and vice versa, comprised in a conveyor 6 suitable for automatically transporting test tubes 1 to and from processing modules, as disclosed in Italian patent application MI2007A002254.

There is also provided the presence of a control unit 7 suitable for coordinating the control devices involved during the load/unload operations and memorising information relating to the handled test tubes.

Figure 2:
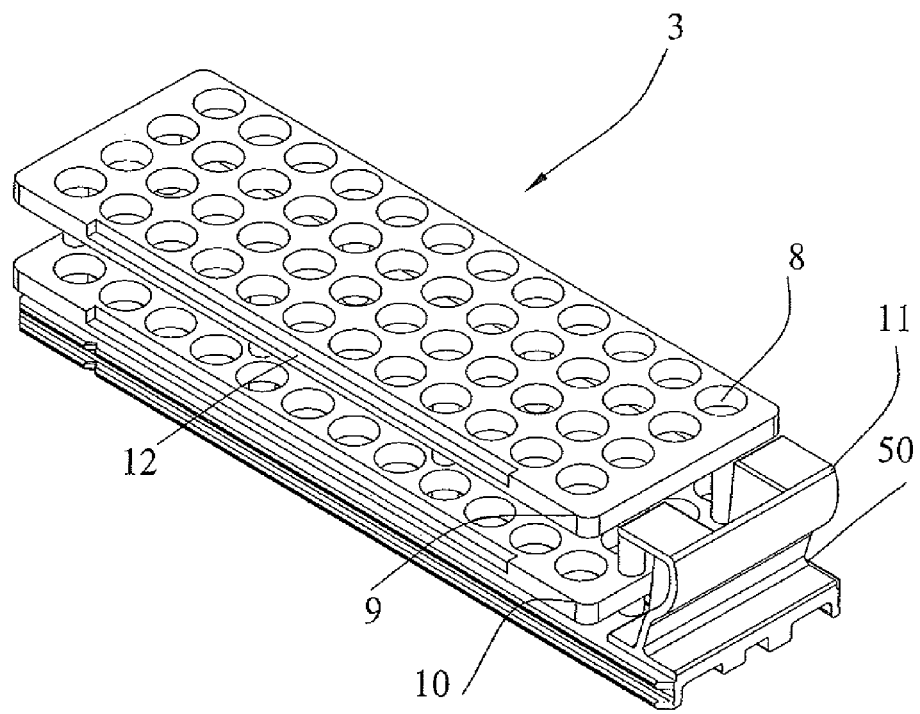
FIG. 2 shows a perspective view of the test-tube rack.

The test-tube rack 3, as shown in FIG. 2, comprises a multitude of locations 8 (in this example there are 48 locations 8 organised in 4 parallel rows 40 of 12 locations each), that are suitable for stably sustaining the test tubes in a perfectly vertical position owing to an upper supporting base 9 and a lower supporting base 10.

The rack 3 further comprises a grip 11 suitable for ensuring manual grasping; during loading it is in fact the operator who manually inserts the test tubes into the locations and positions the thus filled rack 3 on the load/unload bench 2.

Figure 3:
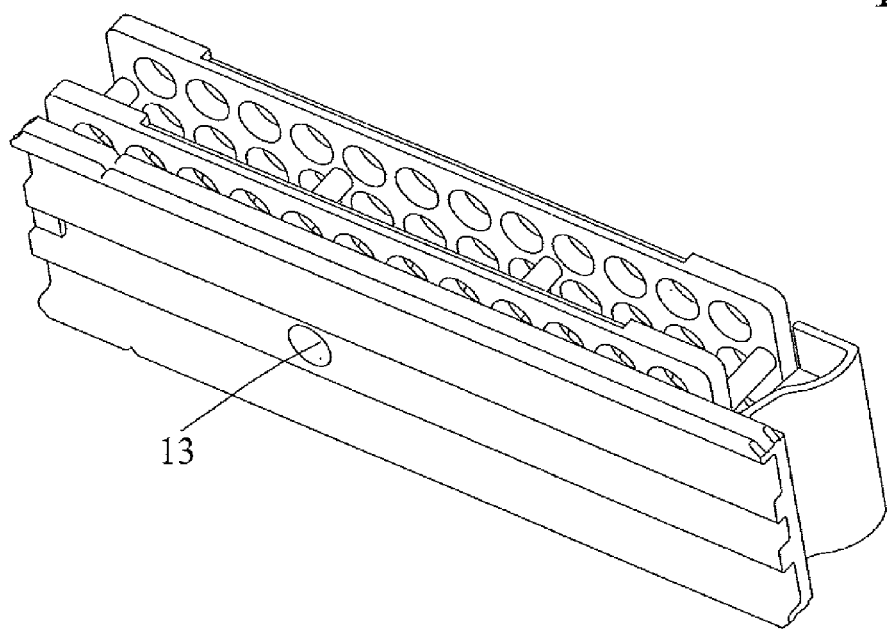
FIG. 3 shows a perspective bottom view of the configuration in FIG. 3.

In order to identify the rack 3, there may be a bar 12 present that is suitable for receiving a barcode that is readable by suitable barcode reading devices when they are present in the apparatus but in general it is preferable to use the transponders 13 positioned at the base of the racks 3, as shown in FIG. 3, memorizing the recognition data of the racks, such as, for example, the unique identification codes for each rack.

Said transponders 13 are suitable for communicating with an identification and control device of RFID type, as will be disclosed below.

Figure 4:
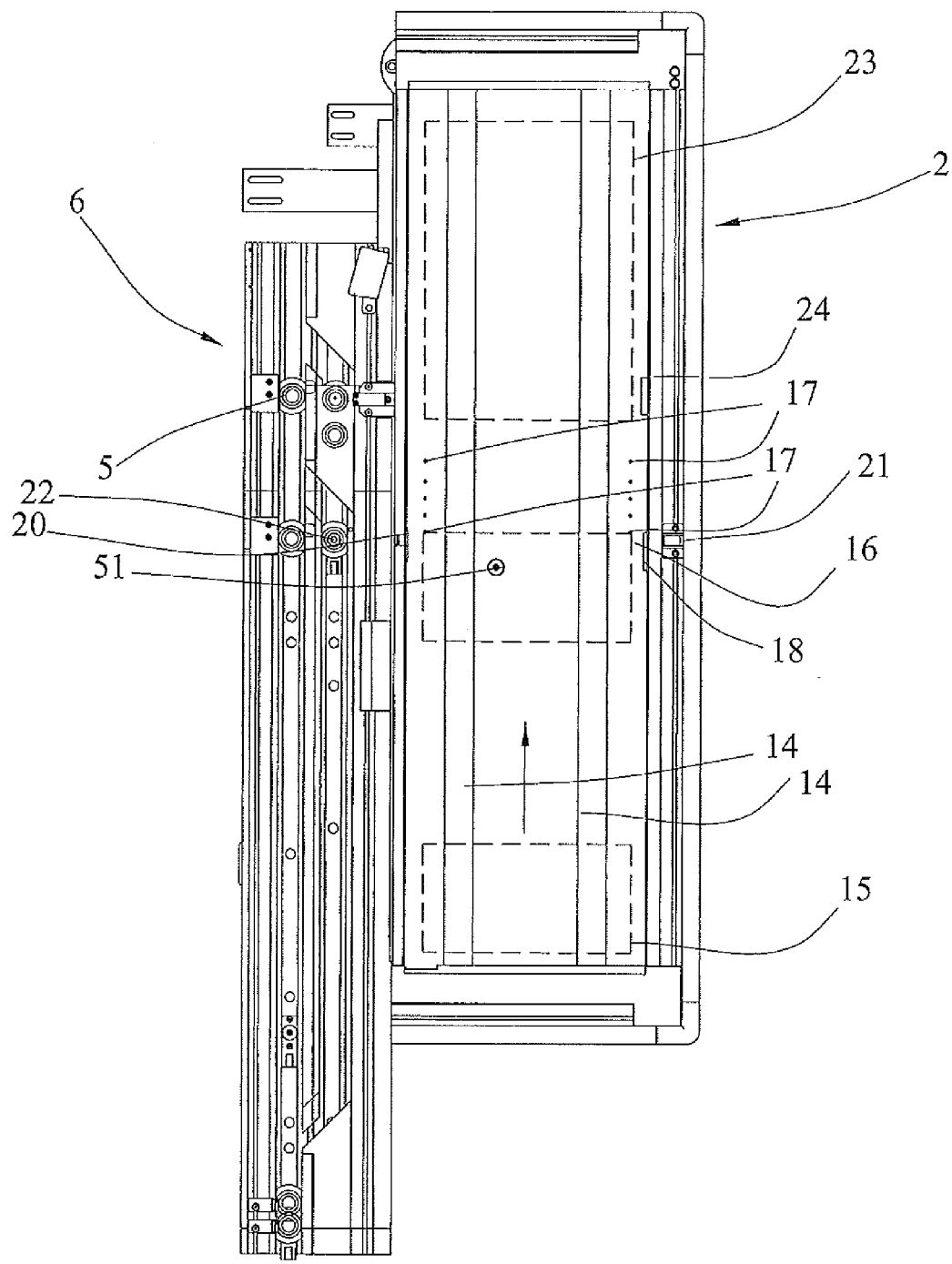
FIG. 4 shows a top view of the bench with the test-tube movement device and the test-tube racks removed from the bench.
Figure 5:
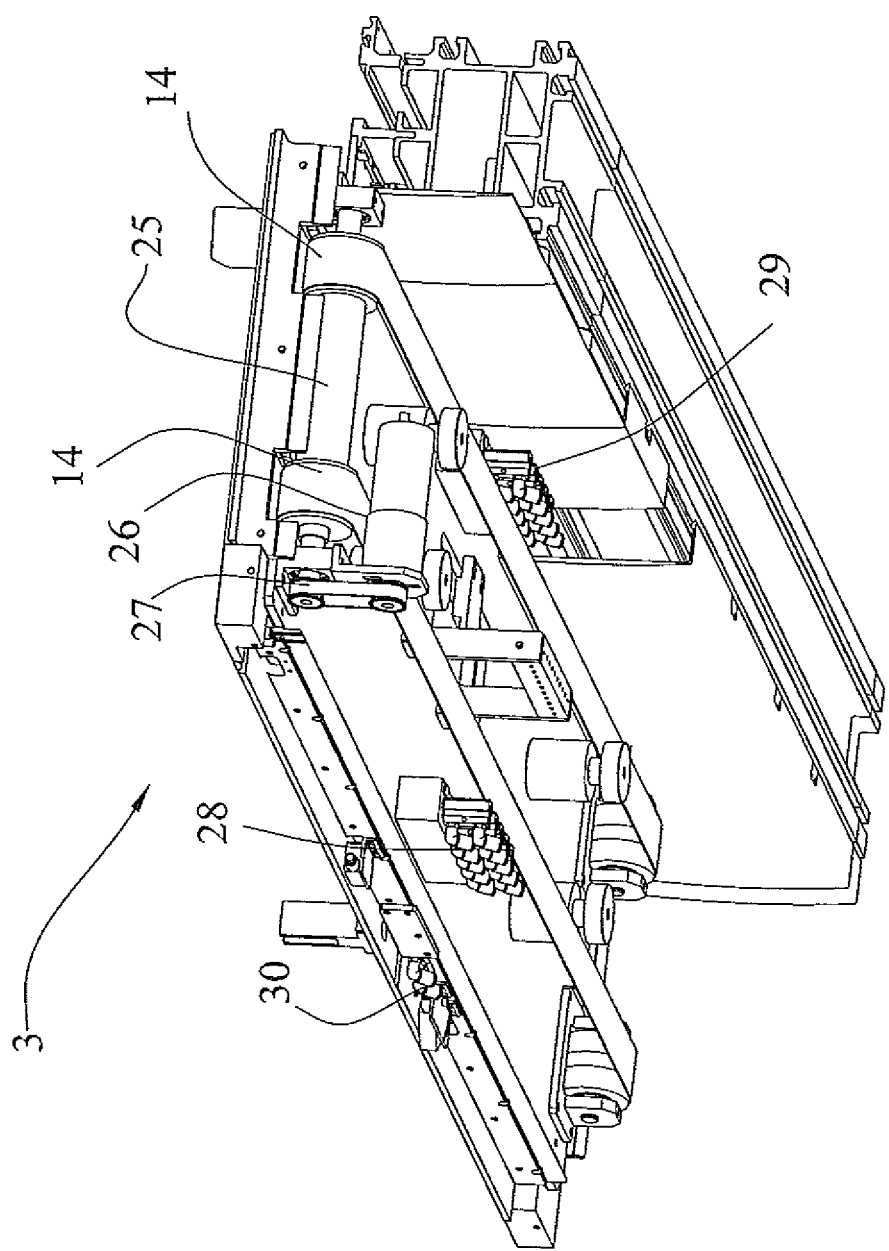
FIG. 5 shows a perspective bottom view of the bench with the guards and supports removed.

In FIG. 4 there is shown the bench 2, interfaced with the conveyor 6, devoid of the racks 3 and of the handling device 4. Said bench 2 comprises a pair of belts 14 that are suitable for running in the direction indicated by the arrow so as to generate the movement, by dragging, of the racks 3 along the direction indicated. Such belts 14 run along a pulley 25 rotated by a motor 26 the movement of which is transmitted by a belt 27 (FIG. 5).

During the loading step, a laboratory operator manually positions a rack 3 loaded with test tubes 1 in the rack loading area 15 (indicated in FIG. 4 by a dashed area).

The pair of belts 14 moves the rack, by dragging, along the running direction, until the rack reaches a first stop position 16 (indicated in FIG. 4 by a second dashed area).

In said stop position 16 there is an identification and control device of RFID type, comprising an antenna 51, suitable for receiving from the transponder 13 present at the base of the racks 3 the rack 3 presence confirmation and a unique code identifying the rack.

The path of the rack 3 is stopped in the stop position 16 by a pair of stop pistons 17 (FIGS. 1 and 4) pneumatically controlled by solenoid valves 28 and 29 (FIG. 5).

Such pairs of stop pistons 17, by exiting from the plane of the bench 2, prevent the rack moving along the direction of the running of the belts.

Memorized in the control unit 7 the unique identifying code identifying the rack 3, a stop device 18 (FIG. 4), exiting from the lateral profile of the bench 2, is positioned in the profile 50 of the rack 3 (FIG. 2), ensuring the stability thereof during possible stress in a vertical direction with respect to the bench 2. The stop device 18 is controlled pneumatically by solenoid valves 30 (FIG. 5).

The presence of test tubes along the first row 40 of the rack is controlled by a barrier constituted by an emitter 20 of a laser beam towards a receiver 21 (FIGS. 1 and 4); if one or more test tubes are present on the first row the laser beam is interrupted and this information is sent to the control unit 7.

As the information on the interruption of the laser beam indicates the presence of test tubes on the row but not the location or the locations engaged, the test tubes handling device 4 is commanded by the control unit 7 to monitor, location by location, the presence of test tubes along the first row.

When the handling device 4 for test tubes meets a test tube, it is moved from the corresponding location to a transport device 5 that is available and free in a load/unload position 22 present on the conveyor 6.

During this process, owing to the detaching movement of the test tube from the location, the rack 3 may undergo stress in a vertical direction; such possible movements in a vertical direction are prevented by the stop device 18 disclosed previously.

After the first row has been monitored, the pair of stop pistons 17 returns to the level of the bench 2 and a second pair of pistons 17 exits, enabling the rack to transferred and be again locked in a second stop position, such that the second row of locations is aligned with the beam of the emitter 20 and the presence of test tubes on such a row can be monitored.

This process is repeated for the other two rows of the rack, using the presence of further pairs of stop pistons 17.

At the time as this rack unloading procedure, a rack loading procedure occurs: the handling device 4 in fact, for each freed rack position, can load a test tube 1 thereupon, moving the test tube from a transport device 5 present in the load/unload position 22 located on the conveyor 6.

The information on the test tubes removed from the conveyor 6 and positioned in the rack 3 and corresponding positions inside the rack are memorised by the control unit 7.

After this load/unload procedure has been terminated, the fourth pair of stop pistons 17 returns to the level of the bench 2, making the rack run on the bench for a short portion until it is locked by a fifth and last pair of pistons 17, the distance of which from the first pair of pistons is the equivalent of the width of a rack. In the moment in which the rack is stopped by the fifth pair of pistons this enables the first pair of pistons to exit. This procedure is necessary inasmuch as if several racks are loaded simultaneously in the loading area 15 they run on the bench in adjacent positions; at the moment in which the fourth pair of pistons releases a rack, if a rack is present in a preceding position, the first pair of pistons is unable to exit to stop said rack, risking the latter being released together with the processed rack.

The rack 3, released by the fifth pair of pistons 17, running on the belts reaches a release or conservation area 23.

In the disclosed embodiment the release area can house up to 5 empty racks.

Presence signallers 24 can be present (FIG. 4), included on the bench 2 inserted into the side profile, suitable for reporting the presence of a rack in the last free position and possibly for interrupting the process.

When the automation installation requires the reprocessing of a test tube unloaded into a rack on the bench, such a test tube can be recovered, the location thereof inside the rack 3 having been memorized, the identification and the position of such rack in the conservation area 23 having been memorized by the control unit 7.

The physical recovery of the test tube is obtained by allowing the belts 14 to run also in an opposite direction to the preceding direction, so as to again move the racks from the conservation zone 23 to the stopping zone 16 and enable the handling device 4 to reach the location in which the required test tube is present. This ensures that the recovery of test tubes occurs at the end of processing of all the test tubes, and i.e. in the moment in which the racks are in the configuration shown in FIG. 1.

The invention claimed is:

1. An apparatus for automatically loading and unloading test tubes, comprising:
   a bench having a bottom surface and lateral sidewalls extending perpendicular to the bottom surface said bench supporting
   a plurality of racks disposed on the bench, each rack containing a plurality of rows of test tubes;
   a plurality of pairs of pistons movable from a lower position inside a plane of the bench, to an extending position outside the plane of the bench, each pair of pistons being independently movable from each other, the extending position of each pair of pistons corresponding to a stop position of a rack which is engaged by said pair of pistons;
   each pair of pistons being spaced apart by a distance equal to a distance between two adjacent rows of each rack;
   a stop device movable from a position at the lateral sidewalls of the bench to a position towards the lateral profile of the rack such that the stop device engages the lateral profile of the rack in order to ensure stability thereof during possible stress in a vertical direction with respect to the bench;
   a pair of belts for conveying the rack along the bench from a rack loading position to said stop positions by respective pairs of piston placed outside said pair of belts and frontally engaging the rack in correspondence of a front profile of the rack with respect to the motion of the belts;

an emitter positioned to detect the presence of the test tubes in each row of the rack; and a handling device disposed above the bench and adapted to move in the up-down direction for moving test tubes between the test tube rack and a transport device configured to accommodate individual test tubes, said transport device being movable on an automatic conveyor, said handling device being positioned to accommodate the longitudinal movement of the rack for the row-by-row loading and unloading operation.

2. A method for automatically loading and unloading test tubes to and from rows of a single rack disposed on a bench using the apparatus of claim 1, the method comprising the following steps:

a) moving a first pair of pistons into an extending position for providing a first stop position;

b) stopping a rack with the first row of pistons;

c) moving a stop device from a position at the sidewalls of the bench to a position towards the lateral profile of the rack such that the stop device engages the lateral profile of the rack in order to ensure stability thereof during possible stress in a vertical direction with respect to the bench;

d) processing a first row of test tubes on the rack;

e) retracting the first pair of pistons after the first row of test tubes has been processed in the first stop position;

f) retracting the stop device to place the stop device at the sidewall of the bench;

g) moving a second pair of pistons to the extending position for providing a second stop position;

h) moving the rack a distance equal to a distance between the first row of test tubes and a second row of test tubes, wherein the first row and second row of test tubes are adjacent, and the rack contacts the second pair of pistons;

i) moving a stop device from a position at the sidewalls of the bench to a position towards the lateral profile of the rack such that the stop device engages the lateral profile of the rack in order to ensure stability thereof during possible stress in a vertical direction with respect to the bench;

j) processing the second row of test tubes on the rack; and k) repeat steps a-j for any subsequent rows of test tubes.

* * * * *